United States Patent [19]

Madala et al.

[11] Patent Number: 6,051,695
[45] Date of Patent: Apr. 18, 2000

[54] PROCESS FOR PREPARING ERYTHROMYCIN DERIVATIVE, SUCH AS ROXITHROMYCIN, FROM THE CORRESPONDING OXIME

[75] Inventors: Murali Krishna Madala; Suresh Babu Meduri; Ketan Dhansukhlal Vyas; Ashok Krishna Kulkarni, all of Mysore, India

[73] Assignee: Max India Limited, Punjab, India

[21] Appl. No.: 09/253,584

[22] Filed: Feb. 19, 1999

[30] Foreign Application Priority Data

Sep. 30, 1998 [IN] India ........................................ 2912/98

[51] Int. Cl.[7] .............................. C07H 1/00; C07H 17/08
[52] U.S. Cl. ............................. 536/7.4; 536/7.2; 536/18.5
[58] Field of Search ............................ 536/7.2, 7.9, 18.5; 514/29

[56] References Cited

U.S. PATENT DOCUMENTS

| 4,349,545 | 9/1982 | Gouin D'Ambrieres et al. | 514/29 |
| 5,808,017 | 9/1998 | Chang | 536/7.4 |

*Primary Examiner*—Elli Peselev
*Attorney, Agent, or Firm*—Ladas & Parry

[57] ABSTRACT

A process for preparing an erythromycin derivative, such as roxithromycin, from the corresponding oxime is disclosed. The oxime is reacted with a metal alkoxide and results in improvements over prior art processes involving the oxime. Roxithromycin is a known anti-bacterial agent.

16 Claims, No Drawings

PROCESS FOR PREPARING ERYTHROMYCIN DERIVATIVE, SUCH AS ROXITHROMYCIN, FROM THE CORRESPONDING OXIME

The present invention relates to an improved process for preparing erythromycin derivatives, in particular that known as roxithromycin, from the corresponding oxime.

Erythromycin derivatives, in particular those of general formula (I) (defined below) disclosed in U.S. Pat. No. 4,349,545, the contents of which are incorporated herein by reference in their entirety, include compounds having antibacterial use. One such compound is known as roxithromycin, namely, 9-(2',5'-dioxahexyloxyimino) erythromycin or 9-[O-[(2-methoxyethoxy)methyl]oxime of erythromycin, which is a compound of formula (I) wherein R is —O(CH$_2$)$_2$—O —CH$_3$, A is —CH$_2$, and R$_a$ is H:

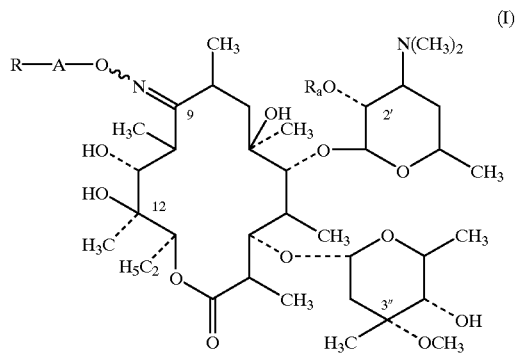

(I)

wherein A is a linear or branched alkylene of 1 to 6 carbon atoms; R is selected from the group consisting of optionally substituted alkoxy of 1 to 6 carbon atoms, optionally substituted alkenyloxy and alkynyloxy of 2 to 6 carbon atoms, optionally substituted alkylthio of 1 to 6 carbon atoms, optionally substituted alkenylthio and alkynylthio of 2 to 6 carbon atoms with the thio groups optionally oxidized to the sulfoxide or sulfone form, optionally substituted aryloxy, and arylthio, optionally substituted aryloxy, and arylthio, optionally substituted aralkyloxy and arylalkylthio, the thio derivatives optionally oxidized to sulfoxide or sulfone, —NR$_1$R$_2$ optionally substituted quaternary ammonium group, halogen, optionally substituted 1,2-epoxyethyl and the group resulting from opening of the epoxy with a nucleophilic reactant, —OOCB, a free or protected formyl, —COOR', thiocyanate, —CN, acyl and carbamoyl, R$_1$ and R$_2$ are individually selected from the group consisting of hydrogen and optionally substituted alkyl of 1 to 6 carbon atoms or taken together with the nitrogen atom to which they are attached from an optionally substituted, optionally unsaturated heterocycle which can contain another heteroatom, B is selected from the group consisting of optionally substituted alkyl and alkoxy of 1 to 6 carbon atoms, optionally substituted aryl and aryloxy and optionally substituted aralkyl and aralkoxy of 1 to 6 alkyl carbon atoms, R' is selected from the group consisting of hydrogen, a cation and an ester group; and R$_a$ is selected from the group consisting of hydrogen and acyl of an organic carboxylic acid of 1 to 18 carbon atoms;

and their non-toxic, pharmaceutically acceptable acid addition salts.

The aforementioned patent specification discloses, inter alia, the preparation of roxithromycin and its analogues by reacting the corresponding 9-oxime of erythromycin with a compound of formula Hal—A—R (wherein A and R as defined for the erythromycin derivative and Hal is a halogen) optionally in the presence of a base. Such bases are stated to be triethylamine; an alkali metal or alkaline earth metal carbonate or bicarbonate; or an alkali metal hydride. The reaction is preferably effected in a polar solvent at from room temperature up to the reflux temperature of the solvent. This is a bi-phasic (liquid/solid) reaction.

However, the disadvantage of such a method is that, besides in practice requiring heating, the reaction time is said to vary from several hours up to several days to go to completion. In practice, according to example 6 of the aforementioned patent specification, a first reaction period of sixteen hours is followed by two further reaction periods of fifteen and eighteen hours, respectively.

Attempts have been made by various workers in this field to provide a more economic and less time-consuming means of carrying out the reaction. Accordingly, Austrian patent specification no 94/151 discloses, inter alia, the conversion of the erythromycin oxime to roxithromycin and its analogues using sodium or potassium carbonate in n-butanol or acetone at a temperature of 50–120° C. Hence, significantly elevated temperatures are still required.

An alternative method has been disclosed in Spanish patent specification no 2 036 472, but this requires the use of an ammonium salt instead of the halide to react with the oxime in a non-alcoholic polar solvent. This is, again, a biphasic (liquid/solid) reaction. On the other hand, Spanish patent specifications nos 2 026 824 and 2 024 371 rely on the use of sodium or potassium hydroxide in the presence of a phase transfer catalyst in another biphasic reaction involving two immiscible liquids.

As well as long reaction times, these known processes involve controlled addition (lot-wise), elaborate work-up and several crystallisations, which makes more difficult the control of large batch production and standardisation of the process.

However, we have surprisingly found that the use of a metal alkoxide as the base in the reaction enables the reaction to proceed more quickly and at a lower temperature than the prior art methods using metal bicarbonates, carbonates or hydroxides.

Accordingly, the present invention provides a process for the preparation of a compound of formula (I), as defined hereinabove, which process comprises reacting a 9-oxime of erythromycin of formula (II):

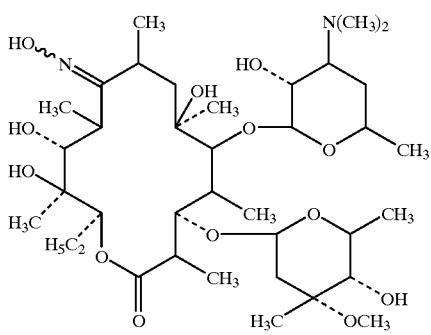

(II)

with a compound of formula (III):

X—A—R          (III)

wherein A and R have the same meaning as in formula (I) and X is a leaving group;
together with a metal alkoxide; and,
optionally thereafter, converting the compound of formula (I) so prepared to any other desired compound of-formula (I) or salt thereof.

Preferably, the reaction is carried out in a single-phase system, particularly, a liquid single-phase system in which the reactants are both in the liquid phase and are mutually miscible.

Preferably, the process is carried out in the presence of an organic, more preferably a polar organic, solvent such as a non-alcoholic solvent. Conveniently, the solvent may be chosen from polar aprotic solvents and halogenated alkanes, ketones, nitrites, esters of organic acids, dimethylformamide (DMF), dimethylsulphoxide, hexamethylphosphotriamide, and ethers such as dialkylethers, tetrahydrofuran and dioxane, and mixtures of these. Especially convenient solvents are those having a low number of carbon atoms in the alkyl chain, such as from 1 to 4, such as acetone, acetonitrile, ethylacetate, diethylether, methylene dichloride, ethylene dichloride and chloroform, and the like. Particularly preferred solvents for use in accordance with the invention are DMF and ethylacetate, especially DMF.

Since one of the advantages of the process according to the present invention is its ability to go to completion in the absence of significantly elevated temperatures, it will be evident that preferred temperatures are as low as possible and do not exceed 50° C. More preferred is when the reaction is carried out at a temperature in the range of from −10–40° C., such as −10–30° C., especially preferred is below room or ambient temperature, such as less than about 20–22° C., more especially in the range of from about 0 to about 10° C.

Depending upon the precise reagents and reaction conditions chosen, especially the temperature, the reaction according to the present invention can surprisingly go to completion in a few hours, such as in up to about 12 hours, more usually in up to about 8 hours, such as in the range of from about 2 to about 6 hours, preferably from about 2 to about 3 hours.

Suitable metal alkoxides for use in accordance with the invention include alkali and alkaline earth metal alkoxides, preferably wherein the alkyl chain has from 1to 4 carbon atoms, such as methoxide, ethoxide, propoxide or butoxide. Examples of suitable metal alkoxides are therefore sodium or potassium methoxide, sodium ethoxide, magnesium ethoxide and potassium t-butoxide. Especially preferred is the use of sodium methoxide.

Suitable compounds of formula (III) include those wherein X is chosen from any of the standard leaving groups known to those skilled in the art. Preferred such leaving groups include those suitable for nucleophilic substitution; especially preferred is halo, such as chloro. A particularly preferred compound of formula (III) is (methoxyethoxy) methyl chloride (MEM.Cl).

Preferred compounds of formula (II) include those wherein $R_a$ is hydrogen. Most preferred is erythromycin 9-oxime.

Therefore, the invention accordingly provides a process for the preparation of roxithromycin, which process comprises reacting erythromycin 9-oxime with methoxyethoxymethyl-X (where X is as defined hereinabove, especially chloride) and a metal alkoxide such as sodium methoxide in the presence of an aprotic polar or halogenated solvent at a temperature below about 50° C., such as at about −10–40° C., for less than about 12 hours, such as for about 2–6 hours. In particular, the present invention provides such a reaction carried out in a single, liquid/liquid phase.

According to a more detailed description of the preferred process of this invention, an erythromycin A oxime (more preferably, 1.0 mole) solution in the organic solvent (more preferably, in a ratio of oxime:solvent in the range of from 1:2.0 to 4.5) is mixed with the alkaline metal alkoxide (more preferably, 1.1–1.8 moles). Controlled addition of (methoxy ethoxy) methyl halide(s) (more preferably 1.0–1.5 mole) over a period of time of about 2 to 6 hrs, preferably 2–3hrs, completes the etherification of the oxygen function in the oxime. Then the organic phase is preferably washed with water or saturated sodium chloride solution and, after complete removal of solvent, the residue can be crystallised, such as from methanol/water or methanol, to get pure roxithromycin directly. In the case of a water-miscible solvent, the work-up will change from removal of the solvent to simply precipitating the product in crude form from the reaction mass by adding water. The precipitate so obtained can then be separated by filtration and crystallised, for example, from methanol/water or methanol.

The process of the present invention, besides also affording the advantage of directly yielding the final product in a substantially pure form, also permits the use of less base and less MEM.Cl in comparison with the prior art processes.

Also, since the etherification reaction in this process proceeds faster than in the prior art processes, the time the erythromycin A oxime or roxithromycin formed remains in the solution phase is significantly less than in the prior art processes. Hence, there is less decomposition, which helps this process to result in nearly quantitative yields.

Furthermore, the process of the present invention has the advantage of permitting large batch production and enables control on stabilisation of yields & reproducibility, with improved time cycles.

The invention therefore further provides the use of a metal alkoxide, such as one hereinbefore described, in the preparation of an erythromycin derivative, such as one hereinbefore described, in particular, roxithromycin, in particular, in a single phase reaction.

The compound of formula (I), such as roxithromycin, thus prepared, may then be formulated, for example, by bringing it into association with a suitable carrier therefor, into a pharmaceutical formulation, as described in the aforementioned patent specifications or otherwise as known to those skilled in the art.

The present invention will now be illustrated by the following example(s).

EXAMPLE 1

Preparation of Roxithromycin using Sodium Methoxide/Ethyl Acetate

Erythromycin A oxime (37.5 g, 0.05 mole) is dissolved in ethyl acetate (115 ml), cooled to 0–5° C. and sodium methoxide (3.24 g, 0.06 mole) added. A solution of (methoxy ethoxy)methyl chloride (6.85 g, 0.055 mole) dissolved in ethyl acetate (20 ml) is slowly added to the above cooled solution with stirring over 2–3 hrs at 0–5° C. The reaction mixture is stirred for 30 min. and completion of the reaction monitored by TLC for the absence of erythromycin A oxime.

The reaction mixture temperature is then raised to ambient, and washed with water and 10% NaCl solution. The organic phase is dried over anhydrous MgSO$_4$ and the solvent is completely removed under vacuum at 50° C. The residue is dissolved in 50 ml of hot methanol, treated with 2.0 g activated charcoal, filtered and washed on a carbon bed with 10 ml hot (50° C.) methanol. The filtrate is gradually cooled to 30° C. and the solution stirred for 6–8 hrs at the same temperature. The crystallised roxithromycin is collected by filtration, and washed and dried at 50–55° C. to obtain a first yield of 25 g (m.p. 119–120° C.) and a second yield of 12.5 g.

EXAMPLE 2

Preparation of Roxithromycin using Sodium Methoxide/DMF

Erythromycin A oxime (37.5 g, 0.05 mole) is dissolved in dimethyl formamide (DMF) (100 ml) and cooled to 0–5° C. Sodium methoxide (3.24 g, 0.062 mole) is added followed by (methoxyethoxy)methyl chloride (6.85 g, 0.055 mole) dissolved in DMF (12.5 ml), slowly with stirring, over 2–3 hours at 0–5° C. The reaction is monitored by TLC until erythromycin A oxime disappears. Then the reaction mixture temperature is raised to ambient and, water (350ml) added over 1 hour. The slurry is stirred for 2 hours, then the crystalline precipitate is collected by filtration and thoroughly washed with water (200 ml).

The resulting wet, crude roxithromycin (65 g) is taken in methanol (75 ml), dissolved by heating and decolourised with activated carbon (2.0 g). The filtrate is cooled slowly to 30° C. and maintained for 6–8 hours. The crystalline product is collected by filtration, and washed and dried at 55° C. The first yield is 30.0 g (m.p. 119–120° C.), and the second yield 7.0 g.

EXAMPLE 3

Preparation of Roxithromycin using Sodium Methoxide/CH$_2$Cl$_2$

Erythromycin A oxime (37.5 g, 0.05 mole) is dissolved in methylene dichloride (337.5 ml), cooled to 0–5° C. and sodium methoxide (3.24 g, 0.06 mole) added. A solution of (methoxyethoxy)methyl chloride (6.85 g, 0.055 mole) dissolved in methylene dichloride (37.5 ml) is slowly added to the above cooled solution under stirring over 2–3 hrs at 0–5° C. The reaction mixture stirred for 30 min. and the end of the reaction monitored by TLC for the absence of erythromycin A oxime.

The reaction mixture temperature is then raised to ambient, and washed with water and saturated NaCl solution. The organic phase is dried over anhydrous MgSO$_4$ for 30 min. and the solvent is completely removed under vacuum at 40° C. The residue is dissolved in methanol (50 ml), treated with activated charcoal (2.0 g), and filtered and washed on a carbon bed with hot methanol (50° C., 10 ml). The filtrate is gradually cooled to 30° C. and the solution stirred for 6–8 hrs at the same temperature. The resulting crystallised roxithromycin is collected by filtration, and washed and dried at 50–55° C. to obtain first yield of 24 g (m.p. 119–120° C.), and a second yield of 11.0 g.

What we claim is:

1. A process for the preparation of a compound of formula (I):

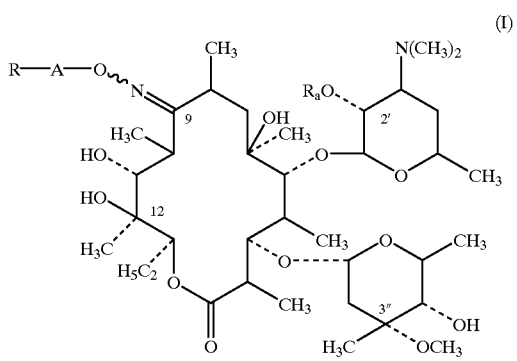

wherein A is a linear or branched alkylene of 1 to 6 carbon atoms;

R is selected from the group consisting of optionally substituted alkoxy of 1 to 6 carbon atoms, optionally substituted alkenyloxy and alkynyloxy of 2 to 6 carbon atoms, optionally substituted alkylthio of 1 to 6 carbon atoms, optionally substituted alkenylthio and alkynylthio of 2 to 6 carbon atoms with the thio groups optionally oxidized to the sulfoxide or sulfone form, optionally substituted aryloxy, and arylthio, optionally substituted aryloxy, and arylthio, optionally substituted aralkyloxy and arylalkylthio, the thio derivatives optionally oxidized to sulfoxide or sulfone, —NR$_1$R$_2$ optionally substituted quaternary ammonium group, halogen, optionally substituted 1,2-epoxyethyl and the group resulting from opening of the epoxy with a nucleophilic reactant, —OOCB, a free or protected formyl, —COOR', thiocyanate, —CN, acyl and carbamoyl, R$_1$ and R$_2$ are individually selected from the group consisting of hydrogen and optionally substituted alkyl of 1 to 6 carbon atoms or taken together with the nitrogen atom to which they are attached form an optionally substituted, optionally unsaturated heterocycle which can contain another heteroatom, B is selected from the group consisting of optionally substituted alkyl and alkoxy of 1 to 6 carbon atoms, optionally substituted aryl and aryloxy and optionally substituted aralkyl and aralkoxy of 1 to 6 alkyl carbon atoms, R' is selected from the group consisting of hydrogen, a cation and an ester group; and $R_a$ is selected from the group consisting of hydrogen and acyl of an organic carboxylic acid of 1 to 18 carbon atoms, or a non-toxic, pharmaceutically acceptable acid addition salt thereof, which process comprises reacting a 9-oxime of an erythromycin derivative of formula (II):

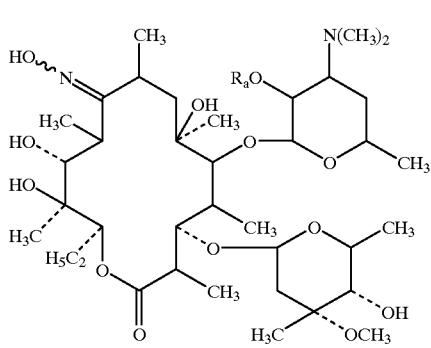

(II)

with a compound of formula (III):

(III)

wherein A and R have the same meaning as in formula (I) and X is a leaving group;

together with a metal alkoxide; and, optionally thereafter, converting the compound of formula (I) so prepared to any other desired compound of formula (I) or salt thereof.

2. A process according to claim 1, wherein R is —O(CH$_2$)$_2$O—CH$_3$, A is —CH$_2$, and $R_a$ is H for the preparation of roxithromycin, namely, 9-(2',5'-dioxahexyloxyimino) erythromycin or 9-[O-[(2-methoxyethoxy)methyl]oxime of erythromycin.

3. A process according to claim 1, wherein the reaction is carried out in a single-phase system.

4. A process according to claim 1, wherein the reaction is carried out in a liquid single-phase system in which the reactants are both in the liquid phase and are mutually miscible.

5. A process according to claim 1 where the reaction is carried out in the presence of an organic solvent chosen from the group consisting of polar aprotic solvents and halogenated alkanes, ketones, nitrites, esters of organic acids dimethylformamide, dimethylsulphoxide, hexamethylphosphotriamide, and ethers and mixtures of these.

6. A process according to claim 1, wherein the reaction is carried out in the presence of an organic solvent selected from the group consisting of acetone, acetonitrile, ethyl acetate, diethylether, methylene dichloride, ethylene dichloride, chloroform and dimethylformamide.

7. A process according to claim 1, wherein the reaction is carried out at a temperature in the range of from −10–40° C.

8. A process according to claim 1, wherein the reaction is carried out at a temperature in the range of from about 0 to about 10° C.

9. A process according to claim 1, wherein the reaction is carried out to completion in the range of from about 2 to about 6 hours.

10. A process according to claim 1, wherein the metal alkoxide is chosen from the group consisting of alkali and alkaline earth metal alkoxides.

11. A process according to claim 1, wherein the metal alkoxide is chosen from the group consisting of sodium and potassium methoxide, sodium ethoxide, magnesium ethoxide and potassium t-butoxide.

12. A process according to claim 1, wherein, in the compound of formula (III), X is chosen from halo.

13. A process according to claim 1, wherein the compound of formula (III) is (methoxyethoxy)methyl chloride.

14. A process according to claim 1, wherein, in the compound of formula (II), $R_a$ is hydrogen.

15. A process according to claim 1, wherein the compound of formula (II) is erythromycin 9-oxime.

16. A process for the preparation of roxithromycin, which process comprises reacting erythromycin 9-oxime with methoxyethoxymethyl-X, wherein X is a leaving group, and a metal alkoxide in the presence of an aprotic polar or halogenated solvent at a temperature below about 50° C., for less than about 12 hours.

\* \* \* \* \*